US007026526B2

(12) United States Patent
Snell (10) Patent No.: US 7,026,526 B2
(45) Date of Patent: Apr. 11, 2006

(54) MULTI-GENE EXPRESSION CONSTRUCTS CONTAINING MODIFIED INTEINS

(75) Inventor: Kristi D. Snell, Belmont, MA (US)

(73) Assignee: Metabolix, Inc., Cambridge, MA (US)

(*) Notice: Subject to any disclaimer, the term of this patent is extended or adjusted under 35 U.S.C. 154(b) by 116 days.

(21) Appl. No.: 09/779,957

(22) Filed: Feb. 9, 2001

(65) Prior Publication Data

US 2002/0129400 A1 Sep. 12, 2002

Related U.S. Application Data

(60) Provisional application No. 60/181,739, filed on Feb. 11, 2000.

(51) Int. Cl.
*C12N 15/29* (2006.01)
*C12N 15/87* (2006.01)
*C12N 5/04* (2006.01)

(52) U.S. Cl. .................. 800/278; 800/287; 800/281; 435/468; 435/419

(58) Field of Classification Search .............. 800/278, 800/287, 281, 279; 536/23.6, 23.1; 435/468, 435/419
See application file for complete search history.

(56) References Cited

U.S. PATENT DOCUMENTS

| 5,004,863 A | 4/1991 | Umbeck |
| 5,015,580 A | 5/1991 | Christou et al. |
| 5,024,944 A | 6/1991 | Collins et al. |
| 5,030,572 A | 7/1991 | Power et al. |
| 5,034,322 A | 7/1991 | Rogers |
| 5,159,135 A | 10/1992 | Umbeck |
| 5,169,770 A | 12/1992 | Chee et al. |
| 5,188,958 A | 2/1993 | Moloney et al. |
| 5,231,019 A | 7/1993 | Paszkowski |
| 5,268,463 A | 12/1993 | Jefferson |

(Continued)

FOREIGN PATENT DOCUMENTS

| EP | 0 486 233 A2 | 5/1992 |
| EP | 0 530 129 A1 | 3/1993 |
| EP | 0 604 662 A1 | 7/1994 |
| WO | WO 91/00917 A1 | 1/1991 |
| WO | WO 93/20216 | 10/1993 |
| WO | WO 94/00977 A1 | 1/1994 |
| WO | WO 95/21249 | 8/1995 |
| WO | WO 98/00557 | 1/1998 |
| WO | WO 98/06854 A1 | 2/1998 |
| WO | WO 98/36078 A1 | 8/1998 |
| WO | WO 99/14313 A1 | 3/1999 |

OTHER PUBLICATIONS

Xu et al 1996, The EMBO Journal 15(19):5146–5153.*
Xu et al 1993 Cell 75:1371–1377.*
Of Ingelbrecht et al 1989, The Plant Cell, 1:671–680.*
Southworth et al., 2000, The Embo Journal 19(18):5019–5026).*
Perler (1998, Cell 92:1–4).*
Evans et al (2000, The Journal of Biological Chemistry 275 (13): 9091–9094).*
Morassutti et al (2002, FEBS 519:141–146).*
Chong et al (The Journal of Biological Chemistry 271:22159–22168, list in IDS).*
Banjoko & Trelease, "Development and application of an in vivo plant peroxisome import system," *Plant Physiol.* 107:1201–08 (1995).
Barton, et al., "*Bacillus thuringienis* δ–enfotoxin expressed in transgenic *Nicotiana tabacum* provides resistance to Lepidopteran insects," *Plant Physiol.* 85:1103–09 (1987).
Bevan, et al., "Structure and transcription of the nopaline synthase gene region of T–DNA," *Nucleic Acids Res.* 11:369–85 (1983).
Brown, et al., "Cloning and characterization of the katB gene of *Pseudomonas aeruginosa* encoding a hydrogen peroxide–inducible catalase: purification of KatB, cellular localization, and demonstration that it is essential for optimal resistance to hydrogen peroxide," *J. Bacteriol.* 177:6536–44 (1995).
Chong, et al., "Protein splicing involving the *Saccharomyces cerevisiae* VMA Intein," *J. Biol. Chem.* 271:22159–22168 (1996).
Chong, et al., "Protein splicing of the *Saccharomyces cerevisiae* VMA Intein without the endonuclease motifs," *J. Biol. Chem.* 272:15587–15590 (1997).

(Continued)

*Primary Examiner*—Elizabeth McElwain
*Assistant Examiner*—Stuart F. Baum
(74) *Attorney, Agent, or Firm*—Pabst Patent Group LLP (57) ABSTRACT

Methods and constructs for the introduction of multiple genes into plants using a single transformation event are described. Constructs contain a single 5' promoter operably linked to DNA encoding a modified intein splicing unit. The splicing unit is expressed as a polyprotein and consists of a first protein fused to an intein fused to a second protein. The splicing unit has been engineered to promote excision of all non-essential components in the polyprotein but prevent the ligation reactions normally associated with protein splicing. Additional genetic elements encoding inteins and additional proteins can be fused in frame to the 5'-terminus of the coding region for the second protein to form a construct for expression of more than two proteins. A single 3' termination sequence, such as a polyadenylation sequence when the construct is to be expressed in eucaryotic cells, follows the last coding sequence. These methods and constructs are particularly useful for creating plants with stacked input traits, illustrated by glyphosate tolerant plants producing BT toxin, and/or value added products, illustrated by the production of polyhydroxyalkanoates in plants.

22 Claims, 4 Drawing Sheets

U.S. PATENT DOCUMENTS

| | | | |
|---|---|---|---|
| 5,276,268 A | 1/1994 | Strauch et al. |
| 5,322,783 A | 6/1994 | Tomes et al. |
| 5,364,780 A | 11/1994 | Hershey et al. |
| 5,416,011 A | 5/1995 | Hinchee et al. |
| 5,420,034 A | 5/1995 | Kridl et al. |
| 5,463,174 A | 10/1995 | Moloney et al. |
| 5,464,765 A | 11/1995 | Coffee et al. |
| 5,472,869 A | 12/1995 | Krzyzek et al. |
| 5,519,164 A | 5/1996 | Müllner et al. |
| 5,527,695 A | 6/1996 | Hodges et al. |
| 5,530,196 A | 6/1996 | Fraley et al. |
| 5,538,877 A | 7/1996 | Lundquist et al. |
| 5,538,880 A | 7/1996 | Lundquist et al. |
| 5,608,152 A | 3/1997 | Kridl et al. |
| 5,629,183 A | 5/1997 | Saunders et al. |
| 5,650,554 A | 7/1997 | Moloney |
| 5,668,298 A | 9/1997 | Waldron et al. |
| 5,750,848 A | 5/1998 | Kruger et al. |
| 5,767,378 A | 6/1998 | Beisen et al. |
| 5,777,200 A | 7/1998 | Ryals et al. |
| 5,834,237 A | 11/1998 | Jacobs et al. |
| 6,011,144 A | 1/2000 | Steinbuchel et al. |

OTHER PUBLICATIONS

Cubitt, et al., "Understanding, improving and using green fluorescent proteins," *Trends Biochem. Sci.* 20(11):448–55 (1995).

Dale & Ow, "Gene transfer with subsequent removal of the selection gene from the host genome," *Proc. Natl. Acad. Sci. USA.* 88(23):10558–62 (1991).

Dasgupta, et al., "Co–ordinated expression of multiple enzymes in different subcellular compartments in plants," *The Plant Journal* 16:107–16 (1998).

Dirusso, "Primary sequence of the *Escherichia coli* fadBA operon, encoding the fatty acid–oxidizing multienzyme complex, indicates a high degree of homology to eucaryotic enzymes," *J. Bacteriol.* 172:6459–68 (1990).

Dmochowska, et al., "Structure and transcriptional control of the *Saccharomyces cerevisiae* POX1 gene encoding acyl–coenzyme A oxidase," *Gene* 88:247–52 (1990).

Falco, et al., "Transgenic canola and soybean seeds with increased lysine," *Bio/Technology* 13:577 (1995).

Fromm, et al., "Inheritance and expression of chimeric genes in the progeny of transgenic maize plants," *Biotechnology* (NY). 8(9):833–39 (1990).

Gasser & Fraley, "Genetically Engineering Plants for Crop Improvement," *Science* 244:1293–1299 (1989).

Hahn, Ph.D. Thesis, University of Minnesota (Feb. 1998).

Haplin, et al., "Self–processing 2A–polyproteins—a system for co–ordinate expression of multiple proteins in transgenic plants," *Plant Journal* 17(4):453–459 (1999).

Hitz, "Economic aspects of transgenic crops which produce novel products," *Current Opinion in Plant Biology* 2:135–38 (1999).

Hoffmann. "The pseudomonas aeruginosa phaG gene product is involved in the synthesis of polyhydroxalkanoic acid consisting of medium–chain–length constituents from non–related carbon resources," *FEMS Microbiology Letters* 184:253–259 (2000).

Huisman, et al., "Metabolism of poly(3–hydroxyalkanoates) (PHAs) by *Pseudomonas oleovorans*. Identification and sequences of genes and function of the encoded proteins in the synthesis and degradation of PHA," *J. Biol. Chem.* 266(4):2191–08 (1991).

Jefferson, et al., "GUS fusions: β–glucuronidase as a sensitive and versatile gene fusion marker in higher plants," *EMBO J.* 6(13):3901–07 (1987).

Kato, et al., "Production of a novel copolyester of 3–hydroxybutyric acid with a medium–chain–length 3–hydroxyalkanoic acids by *Pseudomonas sp.* 61–3 from sugars," *Appl. Microbiol. Biotechnol.* 45:363–70 (1996).

Khoudi, et al., "An alfalfa rubisco small subunit homologue shares cis–acting elements with the regulatory sequences of the RbcS–3A gene from pea," *Gene* 197:343–51 (1997).

Kyozuka, et al., "Anaerobic induction and tissue–specific expression of maize Adh1 promoter in transgenic rice plants and their progeny," *Mol. Gen. Genet.* 228(1–2):40–48 (1991).

Lee, et al., "Biosynthesis of copolyesters consisting of 3–hydroxybutyric acid and medium–chain–length 3–hydroxyalkanoic acids from 1,3–butanediol or from 3–hydroxybutryrate by *Pseudomonas sp.* A33," *Appl. Microbiol. Biotechnol.* 42:901–909 (1995).

Liebergesell & Steinbüchel, "Cloning and nucleotide sequences of genes relevant for biosynthesis of poly(3–hydroxybutyric acid) in *Chromatium vinosum* strain D," *Eur. J. Biochem.* 209:135–50 (1992).

Madison & Huisman, "Metabolic engineering of Poly(3–Hydroxyalkanoates): From DNA to Plastic," *Microbiology and Molecular Biology Reviews* 63:21–53 (1999).

Mcelroy, et al., "Isolation of an efficient actin promoter for use in rice transformation," *Plant Cell.* 2(2):163–71 (1990).

Medberry, et al., "Intra–chromosomal rearrangements generated by Cre–lox site–specific recombination," *Nucl. Acids Res.* 23(3):485–90 (1995).

Moloney, et al., "High efficiency transformation of *Brassica napus* using *Agrobacterium* vectors," *Plant Cell Reports* 8:238–42 (1989).

Odell, et al., "Identification of DNA sequences required for activity of the cauliflower mosaic virus 35S promoter," *Nature* 313(6005):810–12 (1985).

Pang, et al., "An improved green fluorescent protein gene as a vital marker in plants," *Plant Physiol.* 112:893–900 (1996).

Peoples & Sinskey, "Fine structural analysis of the *Zoogloea ramigera* phbA–phbB locus encoding β–ketothiolase and acetoacetyl–CoA reductase: nucleotide sequence of phbB," *Molecular Microbiol.* 3(3):349–57 (1989).

Peoples & Sinskey, "Poly–β–hydroxybutyrate in *Alcaligenes eutrophus* H16," *J. Biol. Chem.* 264:15293–97 (1989).

Peoples & Sinskey, "Poly–β–hydroxybutryte (PHB) Biosynthesis in *Alcaligenes eutrophus* H16," *J. Biol. Chem.* 264(26):15298–303 (1989).

Peoples, et al. "Biosynthetic Thiolase from *Zoogloea ramigera*," *J. Biol. Chem.* 262(1):97–102 (1987).

Perler, "Inbase, the New England biolabs intein database," *Nucleic Acids Research* 27:346–347 (1999).

Perler, et al., "Protein splicing and autoproteolysis mechanics," *Current Opinion in Chemical Biology* 1:292–299 (1997).

Perler, et al., "Protein splicing elements: inteins and exteins—a definition of terms and recommended nomenclature," *Nucleic Acids Research* 22:1125–1127 (1994).

Plant, et al., "Regulation of an *Arabidopsis* oleosin gene promoter in transgenic *Brassica napus*," *Plant Mol. Biol.* 25(2):193–205 (1994).

Rehm, et al., "A new metabolic link between fatty acid de Novo synthesis and polyhydroxyalkanoic acid synthesis," *J. Biol. Chem.* 273:24044–51 (1998).

Rowley & Herman, "The upstream domain of soybean oleosin genes contains regulatory elements similar to those of legume storage proteins," *Biochim. Biophys. Acta.* 1345(1):1–4 (1997).

Sato, et al., "Primary structures of the genes, faoA and faoB, from *Pseudomonas fragi* B–0771 which encode the two subunits of the HDT multienzyme complex involved in fatty acid β–oxidation," *J. Biochem.* 111:8–15 (1992).

Sheen, "Protein phosphatase activity is required for light–inducible gene expression in maize," *J. EMBO* 12:3497–505 (1993).

Slightom, et al., *Proc. Natl. Acad. Sci. 80 USA*:1897–901 (1983).

Sudesh et ., al., "Synthesis, structure and properties of polyhydroxyalkanoates: biological properties," *Prog. Polym. Sci.* 25:1503–1555 (2000).

Suh, et al., "Structure of the amplified 5–enolpyruvylshikimate–3–phosphate synthase gene in glyphosate–resistant carrot cells," *Plant Mol. Biol.* 22:195–205 (1993).

Telenti, et al., "The Mycobacterium xenopi GyrA protein splicing element:characterization of a minimal intein," *J. Bacteriol.* 179:6378–6382 (1997).

Timm & Steinbüchel, "Cloning and molecular analysis of the poly(3–hydroxyalkanoic acid) gene locus of *Pseudomonas aeruginosa* PAO1," *Eur. J. Biochem.* 209(1):15–30 (1992).

Triggs–Raine & Loewen, "Physical characterization of katG, encoding catalase HPI of *Escherichia coli,*" *Gene* 52:121–28 (1987).

Xu & Perler, "The mechanism of protein splicing and its modulation by mutation," *EMBO Journal* 15:5146–5153 (1996).

Xu, et al., "Protein splicing: an analysis of the bmached intermediate and its resolution by succinimide formation," *EMBO Journal* 13:5517–522 (1994).

* cited by examiner

MULTI-GENE EXPRESSION CONSTRUCTS CONTAINING MODIFIED INTEINS

This application claims priority to U.S. Ser. No. 60/181,739 filed Feb. 11, 2000.

BACKGROUND OF THE INVENTION

Genetic engineering of plant crops to produce stacked input traits, such as tolerance to herbicides and insect resistance, or value added products, such as polyhydroxyalkanoates (PHAs), requires the expression of multiple foreign genes. The transitional breeding methodology used to assemble more than one gene within a plant requires repeated cycles of producing and crossing homozygous lines, a process that contributes significantly to the cost and time for generating transgenic plants suitable for field production (Hitz, B. Current Opinion in Plant Biology, 1999, 2, 135–138). This cost could be drastically reduced by the insertion of multiple genes into a plant in one transformation event.

The creation of a single vector containing cassettes of multiple genes, each flanked by a promoter and polyadenylation sequence, allows for a single transformation event but can lead to gene silencing if any of the promoter or polyadenylation sequences are homologous (Matzke, M., Matzke, A. J. M., Scheid, O. M. In Homologous Recombination and Gene Silencing in Plants; Paszkowski, J. Ed. Kluwer Academic Publishers, Netherlands, 1994; pp 271–300). Multiple unique promoters can be employed but coordinating the expression is difficult. Researchers have coordinated the expression of multiple genes from one promoter by engineering ribozyme cleavage sites into multi-gene constructs such that a polycistronic RNA is produced that can subsequently be cleaved into a monocistronic RNA (U.S. Pat. No. 5,519,164). Multiple genes have also been expressed as a polyprotein in which coding regions are joined by protease recognition sites (Dasgupta, S., Collins, G. B., Hunt, A. G. The Plant Journal, 1998, 16, 107–116). A co-expressed protease releases the individual enzymes but often leaves remnants of the protease cleavage site that may affect the activity of the enzymes.

Protein splicing, a process in which an interior region of a precursor protein (an intein) is excised and the flanking regions of the protein (exteins) are ligated to form the mature protein (FIG. 1a), has been observed in numerous proteins from both prokaryotes and eukaryotes (Perler, F. B., Xu, M. Q., Paulus, H. Current Opinion in Chemical Biology 1997, 1, 292–299; Perler, F. B. Nucleic Acids Research 1999, 27, 346–347). The intein unit contains the necessary components needed to catalyze protein splicing and often contains an endonuclease domain that participates in intein mobility (Perler, F. B., Davis, E. O., Dean, G. E., Gimble, F. S., Jack, W. E., Neff, N., Noren, C. J., Thomer, J., Belfort, M. Nucleic Acids Research 1994, 22, 1127–1127). The resulting proteins are linked, however, not expressed as separate proteins.

It is therefore an object of the present invention to provide a method and means for making multi-gene expression constructs especially for expression in plants of multiple, separate proteins.

It is a further object of the present invention to provide a method and means for coordinate expression of genes encoding multiple proteins, or multiple copies of proteins, especially proteins involved in metabolic pathways or pathways to make novel products.

SUMMARY OF THE INVENTION

Methods and constructs for the introduction of multiple genes into plants using a single transformation event are described. Constructs contain a single 5' promoter operably linked to DNA encoding a modified intein splicing unit. The splicing unit is expressed as a polyprotein and consists of a first protein fused to an intein fused to a second protein. The splicing unit has been engineered to promote excision of all non-essential components in the polyprotein but prevent the ligation reactions normally associated with protein splicing. Additional genetic elements encoding inteins and additional proteins can be fused in frame to the 5'-terminus of the coding region for the second protein to form a construct for expression of more than two proteins. A single 3' termination sequence, such as a polyadenylation sequence when the construct is to be expressed in eucaryotic cells, follows the last coding sequence.

These methods and constructs are particularly useful for creating plants with stacked input traits, illustrated by glyphosate tolerant plants producing BT toxin, and/or value added products, illustrated by the production of polyhydroxyalkanoates in plants.

BRIEF DESCRIPTION OF THE FIGURES

FIG. 1A shows splicing of a polyprotein in a native intein splicing unit resulting in ligated exteins and a free intein. FIG. 1B shows splicing of a polyprotein in a modified intein splicing unit resulting in free exteins and inteins. FIG. 1C shows a schematic of a cassette for multi-gene expression consisting of a 5' promoter, a modified intein splicing unit, and a polyadenylation signal. For constructs expressing two enzyme activities fused to one intein, n=1. For constructs expressing more than two enzyme activities and more than one intein, n is greater than 1.

DETAILED DESCRIPTION OF THE INVENTION

Figure 1A:
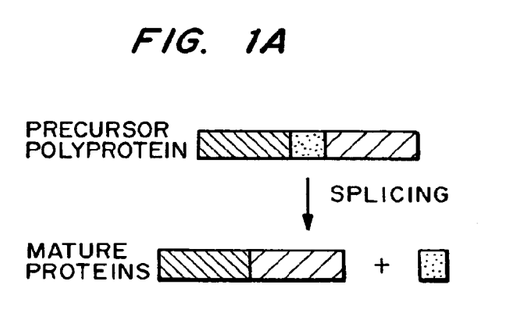
FIGS. 1A, B, and C are schematics showing multi-gene expression using intein sequences.
Figure 1B:
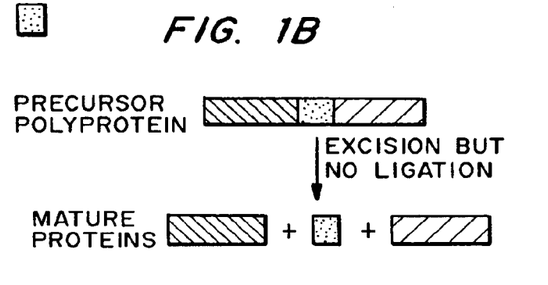
Figure 1C:
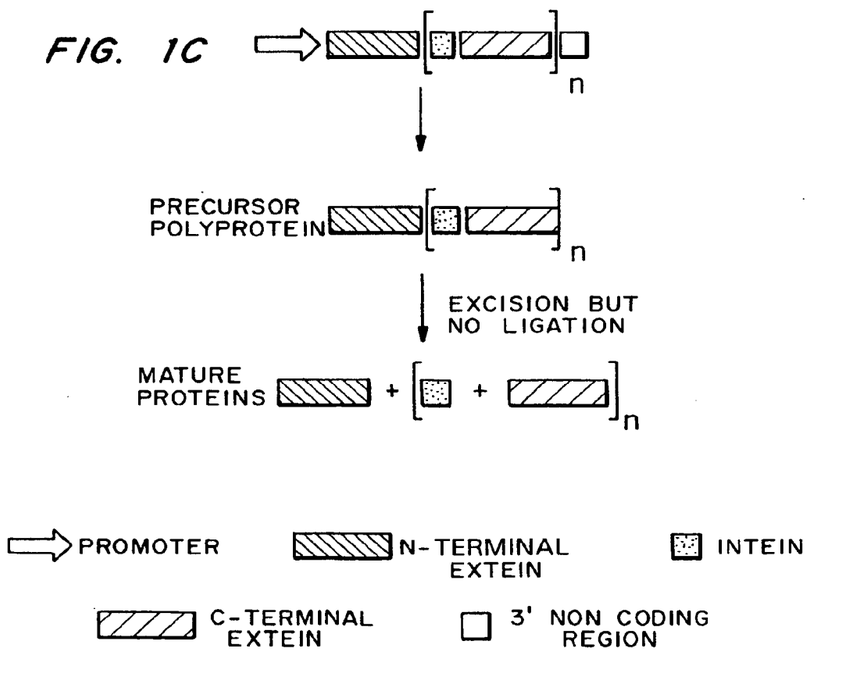

The ability to induce cleavage of a splicing element but prevent ligation of the exteins allows the construction of artificial splicing elements for coordinated multi-protein expression in eukaryotes and prokaryotes (FIG. 1b). The method employs the use of modified intein splicing units to create self-cleaving polyproteins containing more than one, up to several, desired coding regions (FIG. 1c). Processing of the polyprotein by the modified splicing element allows the production of the mature protein units. The described method allows for both coordinated expression of all proteins encoded by the construct with minimal to no alteration of the native amino acid sequences of the encoded proteins, or in some cases, proteins with one modified N-terminal residue. This is achieved by constructing a gene encoding a self-cleavable polyprotein. A modified intein splicing unit, consisting of coding region 1, an intein sequence, and coding region 2, promotes the excision of the polyprotein but prevents the extein ligations of normal intein mediated protein splicing. This arrangement of genes allows the insertion of multiple genes into a cell such as a plant using a single transformation event. The use of this methodology for the insertion and expression of multiple genes encoding metabolic pathways for producing value added products, as well as for engineering plants to express multiple input traits, is described.

I. Constructs for Single Transformation of Multiple Genes

The constructs described herein include a promoter, the coding regions from multiple genes encoding one or more proteins, inteins, and transcription termination sequences. The constructs may also include sequences encoding targeting sequences, such as sequences encoding plastid targeting sequences, or tissue specific sequences, such as seed specific targeting peptides.

The selection of the specific promoters, transcription termination sequences and other optional sequences, such as sequences encoding tissue specific sequences, will be determined in large part by the type of cell in which expression is desired. The may be bacterial, yeast, mammalian or plant cells.

Promoters and Transcription Termination Sequences

A number of promoters for expression in bacterial, yeast, plant or mammalian cells are known and available. The may be inducible, constitutive or tissue specific.

Promoters and transcription termination sequences may be added to the construct when the protein splicing unit is inserted into an appropriate transformation vector, many of which are commercially available. For example, there are many plant transformation vector options available (Gene Transfer to Plants (1995), Potrykus, I. and Spangenberg, G. eds. Springer-Verlag Berlin Heidelberg New York; "Transgenic Plants: A Production System for Industrial and Pharmaceutical Proteins" (1996), Owen, M. R. L. and Pen, J. eds. John Wiley & Sons Ltd. England and Methods in Plant Molecular biology-a laboratory course manual (1995), Maliga, P., Klessig, D. F., Cashmore, A. R., Gruissem, W. and Varner, J. E. eds. Cold Spring Laboratory Press, New York) which are incorporated herein by reference. In general, plant transformation vectors comprise one or more coding sequences of interest under the transcriptional control of 5' and 3' regulatory sequences, including a promoter, a transcription termination and/or polyadenylation signal and a selectable or screenable marker gene. The usual requirements for 5' regulatory sequences include a promoter, a transcription initiation site, and a RNA processing signal.

A large number of plant promoters are known and result in either constitutive, or environmentally or developmentally regulated expression of the gene of interest. Plant promoters can be selected to control the expression of the transgene in different plant tissues or organelles for all of which methods are known to those skilled in the art (Gasser and Fraley, 1989, Science 244; 1293–1299). Suitable constitutive plant promoters include the cauliflower mosaic virus 35S promoter (CaMV) and enhanced CaMV promoters (Odell et al., 1985, Nature, 313: 810), actin promoter (McElroy et al., 1990, Plant Cell 2: 163–171), AdhI promoter (Fromm et al., 1990, Bio/Technology 8: 833–839, Kyozuka et al., 1991, Mol. Gen. Genet. 228: 40–48), ubiquitin promoters, the Figwort mosaic virus promoter, mannopine synthase promoter, nopaline synthase promoter and octopine synthase promoter. Useful regulatable promoter systems include spinach nitrate-inducible promoter, heat shock promoters, small subunit of ribulose biphosphate carboxylase promoters and chemically inducible promoters (U.S. Pat. Nos. 5,364,780, 5,364,780, 5,777,200).

It may be preferable to express the tranagenes only in the developing seeds. Promoters suitable for this purpose include the napin gene promoter (U.S. Pat. Nos. 5,420,034; 5,608,152), the acetyl-CoA carboxylase promoter (U.S. Pat. Nos. 5,420,034; 5,608,152), 2S albumin promoter, seed storage protein promoter, phaseolin promoter (Slightom et al., 1983, Proc. Natl. Acad. Sci. USA 80:1897–1901), oleosin promoter (plant et al., 1994, Plant Mol. Biol, 25: 193–205; Rowley et al., 1997, Biochim. Biophys. Acta. 1345: 1–4; U.S. Pat. No. 5,650,554; PCT WO 93/20216) zein, promoter, glutelin promoter, starch synthase promoter, starch branching enzyme promoter etc.

Alternatively, for some constructs it may be preferable to express the transgene only in the leaf. A suitable promoter for this purpose would include the C4PPDK promoter preceded by the 35S enhancer (Sheen, J. EMBO, 1993, 12, 3497–3505) or any other promoter that is specific for expression in the leaf.

At the extreme 3' end of the transcript, a polyadenylation signal can be engineered. A polyadenylation signal refers to any sequence that can result in polyadenylation of the mRNA in the nucleus prior to export of the mRNA to the cytosol, such as the 3' region of nopaline synthase (Bevan, M., Barnes, W. M., Chilton, M. D. Nucleic Acids Res. 1983, 11, 369–385).

Targeting Sequences

The 5' end of the extein, or transgene, may be engineered to include sequences encoding plastid or other subcellular organelle targeting peptides linked in-frame with the transgene. A chloroplast targeting sequence is any peptide sequence that can target a protein to the chloroplasts or plastids, such as the transit peptide of the small subunit of the alfalfa ribulose-biphosphate carboxylase (Khoudi, et al., Gene 1997, 197, 343–351). A peroxisomal targeting sequence refers to any peptide sequence, either N-terminal, internal, or C-terminal, that can target a protein to the peroxisomes, such as the plant C-terminal targeting tripeptide SKL (Banjoko, A. & Trelease, R. N. Plant Physiol. 1995, 107, 1201–1208).

Inteins

The mechanism of the protein splicing process has been studied in great detail (Chong, et al., *J. Biol. Chem.* 1996, 271, 22159–22168; Xu, M-Q & Perler, F. B. EMBO Journal, 1996, 15, 5146–5153) and conserved amino acids have been found at the intein and extein splicing points (Xu, et al., *EMBO Journal,* 1994, 13 5517–522). The constructs described herein contain an intein sequence fused to the 5'-terminus of the first gene. Suitable intein sequences can be selected from any of the proteins known to contain protein splicing elements. A database containing all known inteins can be found on the World Wide Web (Perler, F. B. *Nucleic Acids Research,* 1999, 27, 346–347). The intein sequence is fused at the 3' end to the 5' end of a second gene. For targeting of this gene to a certain organelle, a peptide signal can be fused to the coding sequence of the gene. After the second gene, the intein-gene sequence can be repeated as often as desired for expression of multiple proteins in the same cell (FIG. 1a, n>1). For multi-intein containing constructs, it may be useful to use intein elements from different sources. After the sequence of the last gene to be expressed, a transcription termination sequence must be inserted.

In the preferred embodiment, a modified intein splicing unit is designed so that it can both catalyze excision of the exteins from the inteins as well as prevent ligation of the exteins. Mutagenesis of the C-terminal extein junction in the *Pyrococcus* species GB-D DNA polymerase was found to produce an altered splicing element that induces cleavage of exteins and inteins but prevents subsequent ligation of the exteins (Xu, M-Q & Perler, F. B. EMBO Journal, 1996, 15, 5146–5153). Mutation of serine 538 to either an alanine or glycine induced cleavage but prevented ligation. Mutation of equivalent residues in other intein splicing units should also prevent extein ligation due to the conservation of amino acids at the C-terminal extein junction to the intein. A preferred intein not containing an endonuclease domain is the *Mycobacterium xenopi* GyrA protein (Telenti, et al. J. Bacteriol. 1997, 179, 6378–6382). Others have been found in nature or have been created artificially by removing the endonuclease domains from endonuclease containing inteins (Chong, et al. J. Biol. Chem. 1997, 272, 15587–15590). In a preferred embodiment, the intein is selected so that it consists of the minimal number of amino acids needed to perform the splicing function, such as the intein from the *Mycobacterium xenopi* GyrA protein (Telenti, A., et al., J. Bacteriol. 1997, 179, 6378–6382). In an alternative embodiment, an intein without endonuclease activity is selected, such as the intein from the *Mycobacterium xenopi* GyrA protein or the Saccharaomyces cerevisiae VMA intein that has been modified to remove endonuclease domains (Chong, 1997).

Further modification of the intein splicing unit may allow the reaction rate of the cleavage reaction to be altered allowing protein dosage to be controlled by simply modifying the gene sequence of the splicing unit.

In another embodiment, the first residue of the C-terminal extein is engineered to contain a glycine or alanine, a modification that was shown to prevent extein ligation with the *Pyrococcus* species GB-D DNA polymerase (Xu, M-Q & Perler, F. B. EMBO Journal, 1996, 15, 5146–5153). In this embodiment, preferred C-terminal exteins contain coding sequences that naturally contain a glycine or an alanine residue following the N-terminal methionine in the native amino acid sequence. Fusion of the glycine or alanine of the extein to the C-terminus of the intein will provide the native amino acid sequence after processing of the polyprotein. In an alternative embodiment, an artificial glycine or alanine is created on the C-terminal extein either by altering the native sequence or by adding an additional amino acid residue onto the N-terminus of the native sequence. In this embodiment, the native amino acid sequence of the protein will be altered by one amino acid after polyprotein processing.

The DNA sequence of the *Pyrococcus* species GB-D DNA Polymerase intein is SEQ ID NO:1. The N-terminal extein junction point is the "aac" sequence (nucleotides 1–3 of SEQ ID NO:1) and encodes an asparagine residue. The splicing sites in the native GB-D DNA Polymerase precursor protein follow nucleotide 3 and nucleotide 1614 in SEQ ID NO:1. The C-terminal extein junction point is the "agc" sequence (nucleotides 1615-1617 of SEQ ID NO:1) and encodes a serine residue. Mutation of the C-terminal extein serine to an alanine or glycine will form a modified intein splicing element that is capable of promoting excision of the polyprotein but will not ligate the extein units.

The DNA sequence of the *Mycobacterium xenopi* GyrA minimal intein is SEQ ID NO:2. The N-terminal extein junction point is the "tac" sequence (nucleotides 1–3 of SEQ ID NO:2) and encodes a tyrosine residue. The splicing sites in the precursor protein follow nucleotide 3 and nucleotide 597 of SEQ ID NO:2. The C-terminal extein junction point is the "acc" sequence (nucleotides 598–600 of SEQ ID NO:2) and encodes a threonine residue. Mutation of the C-terminal extein threonine to an alanine or glycine should form a modified intein splicing element that is capable of promoting excision of the polyprotein but will not ligate the extein units.

Exteins Encoding Proteins

The exteins encode one or more proteins to be expressed. These may be the same protein, where it is desirable to increase the amount of protein expressed. Alternatively, the proteins may be different. The proteins may be enzymes, cofactors, substrates, or have other biological functions. They may act independently or in a coordinated manner. In one embodiment, the extein sequences encode enzymes catalyzing different steps in a metabolic pathway.

A preferred embodiment is where the extein sequences encode enzymes required for the production of polyhydroxyalkanoate biopolymers, as discussed in more detail below. In another embodiment, the extein sequences encode different subunits of a single enzyme or multienzyme complex. Preferred two subunit enzymes include the two subunit PHA synthases, such as the two subunit snythase encoded by phaE and phaC, from *Thiocapsa pfennigii* (U.S. Pat. No. 6,011,144). Preferred multi-enzyme complexes include the fatty acid oxidation complexes.

Figure 2:
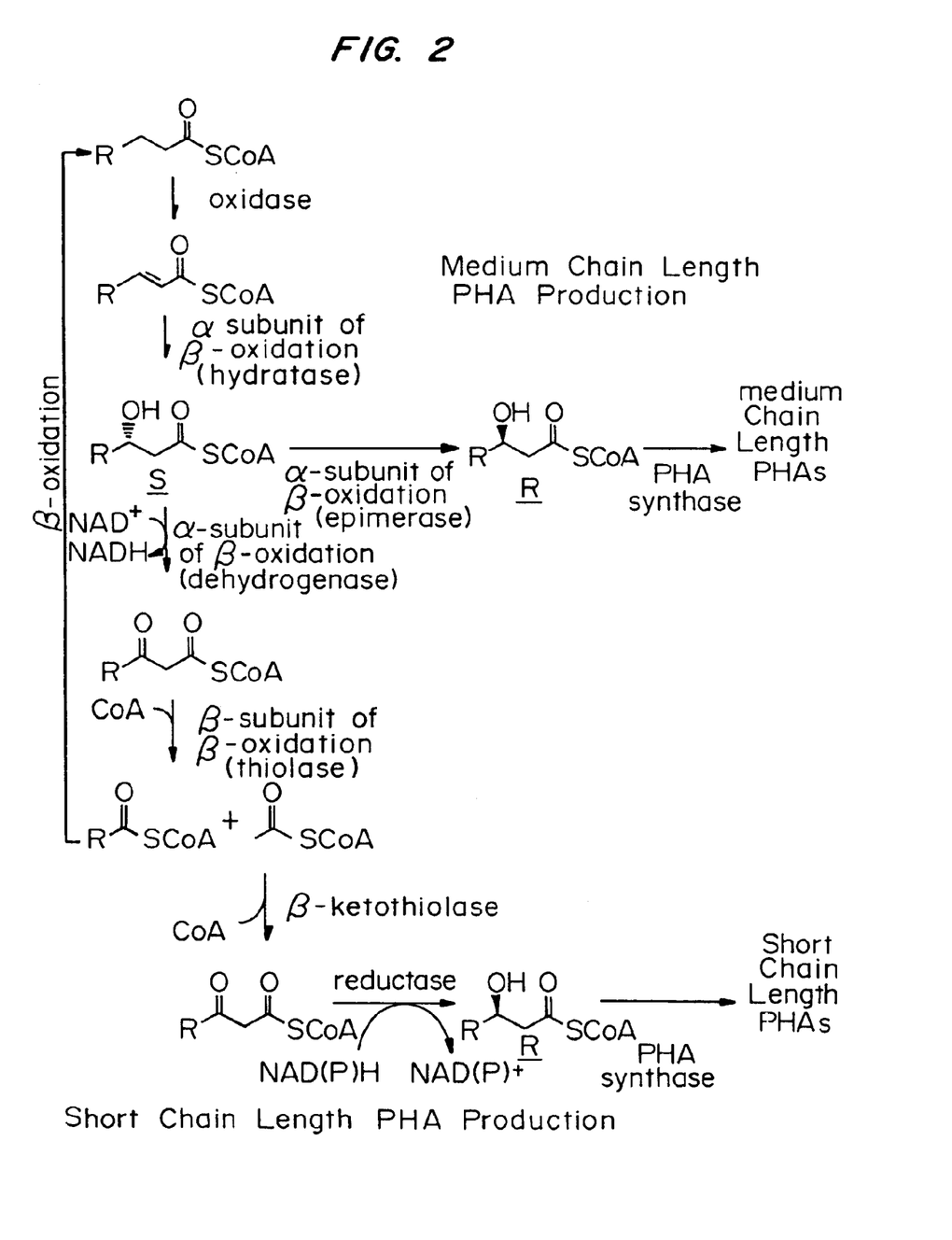
FIG. 2 shows the pathways for short and medium chain length PHA production from fatty acid beta-oxidation pathways. Activities to promote PHA synthesis from fatty acid degradation can be introduced into the host plant by transformation of the plant with a modified splicing unit. Proteins that can be used as exteins in the modified splicing units include acyl CoA dehydrogenases (Reaction 1a), acyl CoA oxidases (Reaction 1b), catalases (Reaction 2), alpha subunits of beta-oxidation (Reactions 3,4,5), beta subunits of beta-oxidation (Reaction 6), PHA synthases with medium chain length substrate specificity (Reaction 7), beta-ketothiolases (Reaction 8), NADH or NADPH dependent reductases (Reaction 9), PHA synthases with short chain length specificity (Reaction 10), and PHA synthases that incorporate both short and medium chain length substrates (Reaction 11).

Enzymes useful for polymer production include the following. ACP-CoA transacylase refers to an enzyme capable of converting beta-hydroxy-acyl ACPs to beta-hydroxy-acyl CoAs, such as the phaG encoded protein from *Pseudomonas putida* (Rehm,et al. J. Biol. Chem. 1998, 273, 24044–24051). PHA synthase refers to a gene encoding an enzyme that polymerizes hydroxyacyl CoA monomer units to form polymer. Examples of PHA synthases include a synthase with medium chain length substrate specificity, such as phaC1 from *Pseudomonas oleovorans* (WO 91/00917; Huisman, et al. J. Biol. Chem. 1991, 266, 2191–2198) or *Pseudomonas aeruginosa* (Timm, A. & Steinbuchel, A. Eur. J. Biochem. 1992, 209, 15–30), the synthase from *Alcaligenes eutrophus* with short chain length specificity (Peoples, O. P. & Sinskey, A. J. J. Biol. Chem. 1989, 264, 15298–15303), or a two subunit synthase such as the synthase from *Thiocapsa pfennigii* encoded by phaE and phaC (U.S. Pat. No. 6,011,144). A range of PHA synthase genes and genes encoding additional steps in PHA biosynthesis are described by Madison and Huisman (1999, Microbiology and Molecular biology Reviews 63:21–53) incorporated herein in its entirety by reference. An alpha subunit of beta-oxidation pertains to a multifunctional enzyme that minimally possesses hydratase and dehydrogenase activities (FIG. 2). The subunit may also possess epimerase and Δ3-cis, Δ2-trans isomerase activities. Examples of alpha subunits of beta-oxidation are FadB from *E. coli* (DiRusso, C. C. J. Bacteriol. 1990, 172, 6459–6468), FaoA from *Pseudomonas fragi* (Sato, S., Hayashi, et al. J. Biochem. 1992, 111, 8–15), and the *E. coli* open reading frame f714 that contains homology to multifunctional α subunits of β-oxidation (Genbank Accession # 1788682). A β subunit of β-oxidation refers to a polypeptide capable of forming a multifunctional enzyme complex with its partner α subunit. The β subunit possesses thiolase activity (FIG. 2). Examples of β subunits are FadA from *E. coli* (DiRusso, C. C. J. Bacteriol. 1990, 172, 6459–6468), FaoB from *Pseudomonas fragi* (Sato, S., Hayashi, M., Imamura, S., Ozeki, Y., Kawaguchi, A. J. Biochem. 1992, 111, 8–15), and the *E. coli* open reading frame f436 that contains homology to α subunits of β-oxidation (Genbank Accession # AE000322; gene b2342). A reductase refers to an enzyme that can reduce β-ketoacyl CoAs to R-3-OH-acyl CoAs, such as the NADH dependent reductase from *Chromatium vinosum* (Liebergesell, M., & Steinbuchel, A. Eur. J. Biochem. 1992, 209, 135–150), the NADPH dependent reductase from *Alcaligenes eutropus* (Peoples, 0. P. & Sinskey, A. J. J. Biol. Chem. 1989, 264, 15293–15297), or the NADPH reductase from *Zoogloea ramigera* (Peoples, O. P., Masamune, S., Walsh, C. T., Sinskey, A. J. J. Biol. Chem. 1987, 262, 97–102; Peoples, O. P. & Sinskey, A. J. J. Molecular Microbiology 1989, 3, 349–357). A beta-ketothiolase refers to an enzyme that can catalyze the conversion of acetyl CoA and an acyl CoA to a β-ketoacyl CoA, a reaction that is reversible (FIG. 2). An example of such a thiolase is PhaA from *Alcaligenes eutropus* (Peoples, O. P. & Sinskey, A. J. J. Biol. Chem. 1989, 264, 15293–15297). An acyl CoA oxidase refers to an enzyme capable of converting saturated acyl CoAs to Δ2 unsaturated acyl CoAs (FIG. 2). Examples of acyl CoA oxidases are POX1 from *Saccharomyces cerevisiae* (Dmochowska, et al. Gene, 1990, 88, 247–252) and ACX1 from *Arabidopsis thaliana* (Genbank Accession # AF057044). A catalase refers to an enzyme capable of converting hydrogen peroxide to hydrogen and oxygen. Examples of catalases are KatB from *Pseudomonas aeruginosa* (Brown, et al., J. Bacteriol. 1995, 177, 6536–6544) and KatG from *E. coli* (Triggs-Raine, B. L. & Loewen, P. C. Gene 1987, 52, 121–128).

Multi step enzyme pathways have now been elaborated for the biosynthesis of PHA copolymers from normal cellular metabolites and are particularly suited to the invention described herein. Pathways for incorporation of 3-hydroxyvalerate are described by Gruys et al., in PCT WO 98/00557, incorporated herein by reference. Pathways for incorporation of 4-hydroxybutyrate are elaborated in PCT WO 98/36078 to Dennis and Valentin and PCT WO 99/14313 to Huisman et al. both references are incorporated herein by reference.

In another embodiment, the protein coding sequences encode proteins which impart insect and pest resistance to the plant, as discussed in more detail below. In the case of a protein coding for insect resistance, a *Bacillus thuringensis* endotoxin is preferred, in the case of a herbicide resistance gene, the preferred coding sequence imparts resistance to glyphosate, sulphosate or Liberty herbicides.

Marker Genes

Selectable marker genes for use in plants include the neomycin phosphotransferase gene nptII (U.S. Pat. Nos. 5,034,322, 5,530,196), hygromycin resistance gene (U.S. Pat. No. 5,668,298), and the bar gene encoding resistance to phosphinothricin (U.S. Pat. No. 5,276,268). EP 0 530 129 A1 describes a positive selection system which enables the transformed plants to outgrow the non-transformed lines by expressing a transgene encoding an enzyme that activates an inactive compound added to the growth media. U.S. Pat. No. 5,767,378 describes the use of mannose or xylose for the positive selection of transgenic plants. Screenable marker genes useful for practicing the invention include the beta-glucuronidase gene (Jefferson et al., 1987, EMBO J. 6: 3901–3907; U.S. Pat. No. 5,268,463) and native or modified green fluorescent protein gene (Cubitt et al., 1995, Trends Biochem Sci. 20: 448–455; Pan et al., 1996, Plant Physiol. 112: 893–900). Some of these markers have the added advantage of introducing a trait e.g. herbicide resistance into the plant of interest providing an additional agronomic value on the input side.

II. Methods for Using the Constructs

Multiple uses have been described for intein containing protein splicing elements including affinity enzyme purification and inactivation of protein activity (U.S. Pat. No. 5,834,237). To date, there is no description of the use of intein sequences for coordinated multi-gene expression, a task that is particularly useful in plants for the expression of multiple genes to enhance input traits, or for multi-gene expression for the formation of natural or novel plant products or plants with multiple stacked input traits.

Although means for transforming cells of all types are known, and the constructs described herein can be used in these different cell types, only the transformation of plant cells using these constructs is described in detail. Those skilled in the would be able to use this information to transform the other cell types for similar purposes.

Transformation of Plants

Particularly useful plant species include: the *Brassica* family including *napus, rappa*, sp. *carinata* and *juncea*, maize, soybean, cottonseed, sunflower, palm, coconut, safflower, peanut, mustards including *Sinapis alba* and flax. Suitable tissues for transformation using these vectors include protoplasts, cells, callus tissue, leaf discs, pollen, meristems etc. Suitable transformation procedures include *Agrobacterium*-mediated transformation, biolistics, microinjection, electroporation, polyethylene glycol-mediated protoplast transformation, liposome-mediated transformation, silicon fiber-mediated transformation (U.S. Pat. No. 5,464,765) etc. (Gene Transfer to Plants (1995), Potrykus, I. and Spangenberg, G. eds. Springer-Verlag Berlin Heidelberg New York; "Transgenic Plants: A Production System for Industrial and Pharmaceutical Proteins" (1996), Owen, M. R. L. and Pen, J. eds, John Wiley & Sons Ltd. England and Methods in Plant Molecular Biology—a laboratory course manual (1995), Maliga P., Klessig, D. F., Cashmore, A. R., Gruissem, W. and Varner, J. E. eds. Cold Spring Laboratory Press, New York). *Brassica napus* can be transformed as described for example in U.S. Pat. Nos. 5,188,958 and 5,463,174. Other *Brassica* such as *rappa, carinata* and *juncea* as well as *Sinapis alba* can be transformed as described by Moloney et al. (1989, Plant Cell Reports 8: 238–242). Soybean can be transformed by a number of reported procedures (U.S. Pat. Nos. 5,015,580; 5,015,944; 5,024,944; 5,322,783; 5,416,011; 5,169,770).

A number of transformation procedures have been reported for the production of transgenic maize plants including pollen transformation (U.S. Pat. No. 5,629,183), silicon fiber-mediated transformation (U.S. Pat. No. 5,464,765), electroporation of protoplasts (U.S. Pat. Nos. 5,231,019; 5,472,869; 5,384,253), gene gun (U.S. Pat. Nos. 5,538,877; 5,538,880), and *Agrobacterium*-mediated transformation (EP 0 604 662 A1; WO 94/00977). The *Agrobacterium*-mediated procedure is particularly preferred as single integration events of the transgene constructs are more readily obtained using this procedure which greatly facilitates subsequent plant breeding. Cotton can be transformed by particle bombardment (U.S. Pat. Nos. 5,004,863; 5,159,135). Sunflower can be transformed using a combination of particle bombardment and *Agrobacterium* infection (EP 0 486 233 A2; U.S. Pat. No. 5,030,572). Flax can be transformed by either particle bombardment or Agrobacterium-mediated transformation. Recombinase technologies which are useful in practicing the current invention include the cre-lox, FLP/FRT and Gin systems. Methods by which these technologies can be used for the purpose described herein are described for example in (U.S. Pat. No. 5,527,695; Dale And Ow, 1991, Proc. Natl. Acad. Sci. USA 88: 10558–10562; Medberry et al., 1995, Nucleic Acids Res. 23: 485–490).

Following transformation by any one of the methods described above, the following procedures can be used to obtain a transformed plant expressing the transgenes: select the plant cells that have been transformed on a selective medium; regenerate the plant cells that have been transformed to produce differentiated plants; select transformed plants expressing the transgene at such that the level of desired polypeptide(s) is obtained in the desired tissue and cellular location.

Producing Plants Containing Value Added Products.

The expression of multiple enzymes is useful for altering the metabolism of plants to increase, for example, the levels of nutritional amino acids (Falco et. al., 1995, Bio/Technology 13: 577), to modify lignin metabolism, to modify oil compositions (Murphy, 1996, TIBTECH 14: 206–213), to modify starch biosynthesis, or to produce polyhydroxyalkanoate polymers (PHAs, Huisman and Madison, 1999, Microbiol and Mol. Biol. Rev. 63: 21–53; and references therein).

Modification of plants to produce PHA biopolymers is an example of how these constructs can be used. The PHA biopolymers encompass a broad class of polyesters with different monomer compositions and a wide range of physical properties (Madison and Huisman, 1999; Dudesh et., al., 2000, Prog. Polym. Sci. 25: 1503–1555). Short chain, medium chain, as well as copolymers of short and medium chain length PHAs can be produced in plants by manipulating the plant's natural metabolism to produce 3-hydroxyacyl CoAs, the substrate of the PHA synthase, in the organelle in which polymer is to be accumulated. This often requires the expression of two or more recombinant proteins, with an appropriate organelle targeting signal attached. The proteins can be coordinately expressed as exteins in a modified splicing unit introduced into the plant via a single transformation event. Upon splicing, the mature proteins are released from the intein.

In bacteria, each PHA group is produced by a specific pathway. In the case of the short pendant group PHAs, three enzymes are involved, a beta-ketothiolase (FIG. 2, Reaction 8), an acetoacetyl-CoA reductase (FIG. 2, Reaction 9), and a PHA synthase (FIG. 2, Reaction 10). Short chain length PHA synthases typically allow polymerization of C3–C5 hydroxy acid monomers including both 4-hydroxy and 5-hydroxy acid units. This biosynthetic pathway is found in a number of bacteria such as *Ralstonia eutropha, Alcaligenes latus, Zoogloea ramigera*. etc (Madison, L. L. & Huisman, G. W. Microbiology and Molecular Biology Reviews 1999, 63, 21–53). Activities to promote short chain length PHA synthesis can be introduced into a host plant via a single transformation event with a modified splicing unit in which the exteins are selected from the enzymes described in Reactions 8–10 (FIG. 2). If necessary, genes encoding exteins can be fused to a DNA sequence encoding a peptide targeting signal that targets the mature protein after splicing to a particular compartment of the cell.

Figure 3:
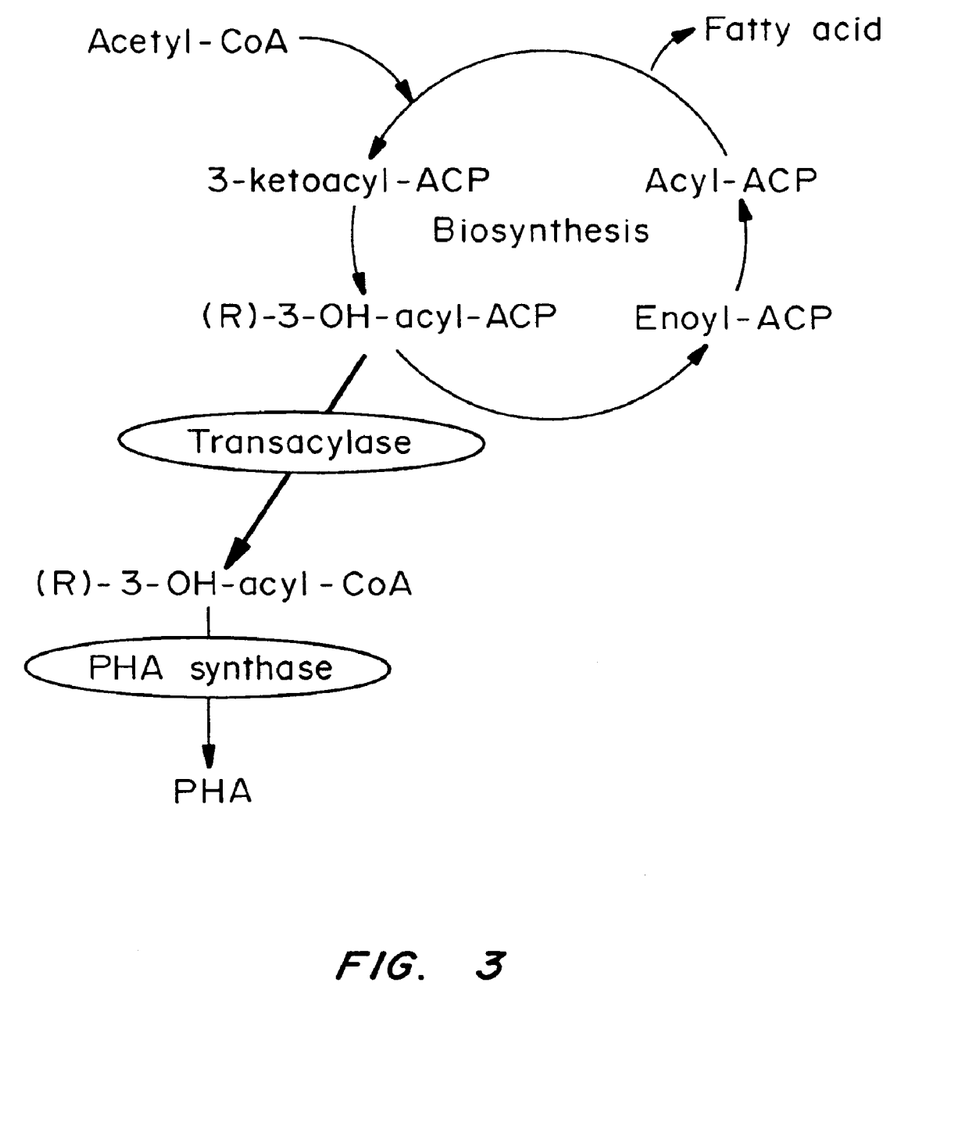
FIG. 3 is a schematic of the pathway for medium chain length PHA production from fatty acid biosynthesis. Activities to promote PHA synthesis from fatty acid biosynthesis can be introduced into the host plant by transformation of the plant with a modified splicing unit. Proteins that can be used as exteins in the modified splicing units include enzymes encoded by the phaG locus (Reaction 1), medium chain length synthases (Reaction 2), beta-ketothiolases (Reaction 3), NADH or NADPH dependent reductases (Reaction 4), and PHA synthases that incorporate both short and medium chain length substrates (Reaction 5).

Medium chain length pendant group PHAs are produced by many different Pseudomonas bacteria. The hydroxyacyl-coenzyme A monomeric units can originate from fatty acid beta-oxidation (FIG. 2) and fatty acid biosynthetic pathways (FIG. 3). The monomer units are then converted to polymer by PHA synthases which have substrate specificity's favoring the larger C6–C14 monomeric units (FIG. 2, Reaction 7; FIG. 3, Reaction 2; Madison, L. L. & Huisman, G. W. Microbiology and Molecular Biology Reviews 1999, 63, 21–53). Activities to promote medium chain length PHA synthesis from fatty acid beta-oxidation pathways can be introduced into a host plant via a single transformation event with a modified splicing unit in which the exteins are selected from the enzymes described in Reactions 1–7 (FIG. 2). If necessary, genes encoding exteins can be fused to a DNA sequence encoding a peptide targeting signal that targets the mature protein after splicing to a particular compartment of the cell.

An enzymatic link between PHA synthesis and fatty acid biosynthesis has been reported in both *Pseudomonas putida* and *Pseudomonas aeruginosa* (Reaction 1, FIG. 3). The genetic locus encoding the enzyme believed to be responsible for diversion of carbon from fatty acid biosynthesis was named phaG (Rehm,et al. J. Biol. Chem. 1998, 273, 24044–24051; WO 98/06854; U.S. Pat. No. 5,750,848; Hoffman, N., Steinbuchel, A., Rehm, B. H. A. FEMS Microbiology Letters, 2000, 184, 253–259). No polymer, however, has been observed upon expression of a medium chain length synthase and PhaG in *E. coli* (Rehm, et al. J. Biol. Chem. 1998, 273, 24044–24051) suggesting that another enzyme may be required in non-native PHA producers such as *E. coli* and plants. Activities to promote medium chain length PHA synthesis from fatty acid biosynthesis pathways can be introduced into a host plant via a single transformation event with a modified splicing unit in which the exteins are selected from the enzymes described in Reactions 1–2 (FIG. 3). If necessary, genes encoding exteins can be fused to a DNA sequence encoding a peptide targeting signal that targets the mature protein after splicing to a particular compartment of the cell.

Co-polymers comprised of both short and medium chain length pendant groups can also be produced in bacteria possessing a PHA synthase with a broad substrate specificity (Reaction 11, FIG. 2; Reaction 5, FIG. 3). For example, *Pseudomonas* sp. A33 (Appl. Microbiol. Biotechnol. 1995, 42, 901–909), *Pseudomonas* sp. 61–3 (Kato, et al. Appl. Microbiol. Biotechnol. 1996, 45, 363–370), and *Thiocapsa pfennigii* (U.S. Pat. No. 6,011,144) all possess PHA synthases that have been reported to produce co-polymers of short and medium chain length monomer units. Activities to promote formation of co-polymers of both short and medium chain length pendant groups can be introduced into a host plant via a single transformation event with a modified splicing unit in which the exteins are selected from the enzymes described in Reactions 1–11 (FIG. 2) for fatty acid degradation routes, and Reactions 1–5 (FIG. 3) for fatty acid biosynthesis routes. If necessary, genes encoding exteins can be fused to a DNA sequence encoding a peptide targeting signal that targets the mature protein after splicing to a particular compartment of the cell.

Additional pathways for incorporation of 3-hydroxyvalerate are described by Gruys et. al., in PCT WO 98/00557, incorporated herein by reference. Pathways for incorporation of 4-hydroxybutyrate are elaborated in PCT WO 98/36078 to Dennis and Valentin and PCT WO 99/14313 to Huisman et. al., incorporated herein by reference.

Prior to producing PHAs from plants on an industrial scale, optimization of polymer production in crops of agronomic value will need to be achieved. Preliminary studies in some crops of agronomic value have been performed including PHB production in maize cell suspension cultures and in the peroxisomes of intact tobacco plants (Hahn, J. J., February 1998, Ph.D. Thesis, University of Minnesota) as well as PHB production in transgenic canola and soybean seeds (Gruys et al., PCT WO 98/00557). In these studies, the levels of polymer observed were too low for economical production of the polymer. Optimization of PHA production in crops of agronomic value will utilize the screening of multiple enzymes, targeting signals, and sites of production until a high yielding route to the polymer with the desired composition is obtained. This is a task which can be simplified if multiple genes can be inserted in a single transformation event. The creation of multi-gene expression constructs is useful for reducing the complexity of the traditional breeding methodology required to make the transgenic plant agronomically useful.

Producing Plants Containing Multiple Stacked Input Traits.

The production of a plant that is tolerant to the herbicide glyphosate and that produces the *Bacillus thuringiensis* (BT) toxin is illustrative of the usefulness of multi-gene expression constructs for the creation of plants with stacked input traits. Glyphosate is a herbicide that prevents the production of aromatic amino acids in plants by inhibiting the enzyme 5-enolpyruvylshikimate-3-phosphate synthase (EPSP synthase). The overexpression of EPSP synthase in a crop of interest allows the application of glyphosate as a weed killer without killing the genetically engineered plant (Suh, et al., J. M Plant Mol. Biol. 1993, 22, 195–205). BT toxin is a protein that is lethal to many insects providing the plant that produces it protection against pests (Barton, et al. Plant Physiol. 1987, 85, 1103–1109). Both traits can be introduced into a host plant via a single transformation even with a modified splicing unit in which the exteins are EPSP synthase and BT toxin.

The present invention will be further understood by reference to the following non-limiting examples.

EXAMPLE 1

In Vivo Expression of two Proteins from an Intein Containing Multi-gene Expression Construct with only one Promoter and one Poly-adenylation Signal in Plant Protoplast Transient Expression Assays.

Figure 4:
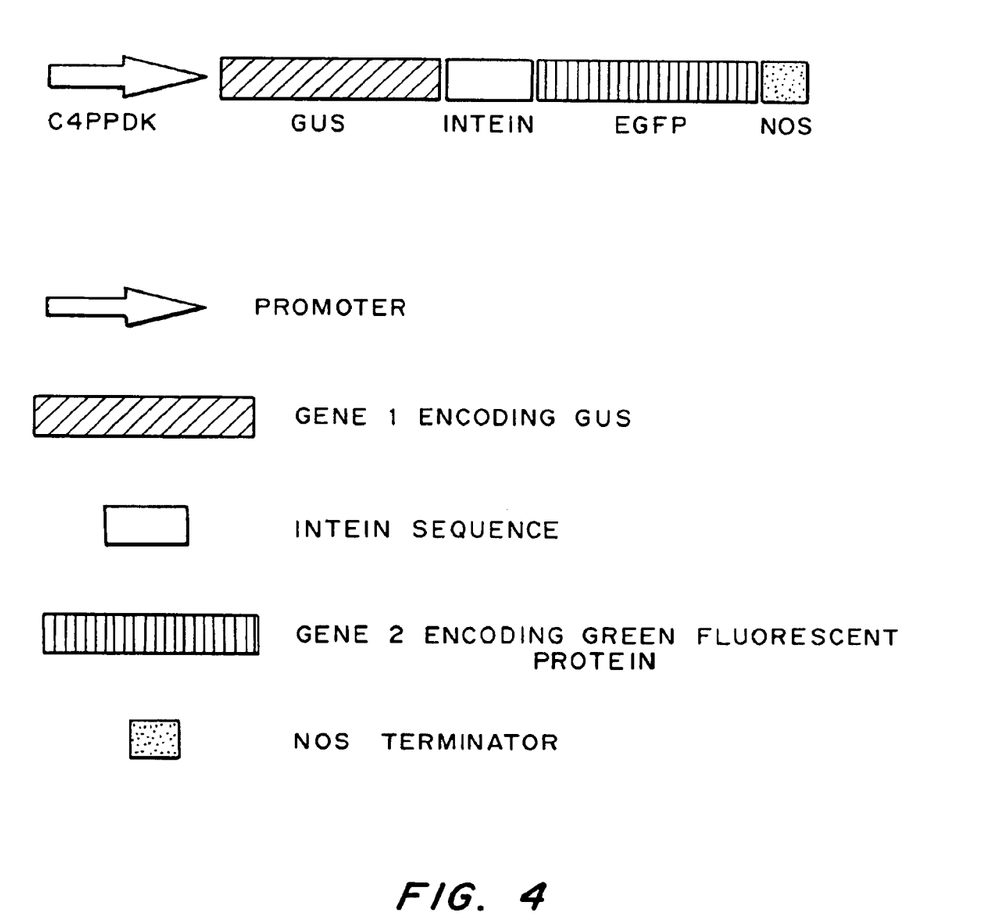
FIG. 4. Plant expression cassette for testing polyprotein processing in *Arabidopsis* protoplasts.

A suitable construct contains the following genetic elements (FIG. 4): a promoter active in leaves such as the 35S-C4PPDK light inducible plant promoter (Sheen, J. EMBO, 1993, 12, 3497–3505); an N-terminal extein sequence encoding beta-glucuronidase (GUS) (Jefferson, R. A., Kavanagh, T. A., Bevan, M. W., EMBO J. 1987, 6, 3901–3907) fused at its C-terminus to the N-terminus of an intein sequence; an intein sequence from the *Pyrococcus* species GB-D polymerase (Xu, M-Q & Perler, F. B. EMBO Jounal, 1996, 15, 5146–5153) in which serine 538 has been mutated to alanine or glycine; a 5'-terminal extein sequence encoding an enhanced green fluorescent protein (EGFP; Clontech, Palo Alto, Calif.) fused at its 3'-terminus to the 5'-terminus of the intein sequence; and a polyadenylation signal.

Production of the correctly spliced GUS and EGFP proteins from a modified intein containing polyprotein construct can be tested using the following protoplast transient expression procedure. Two well-expanded leaves from 4–6 week old plants of *Arabidopsis thaliana* are harvested and the leaves are cut perpendicularly, with respect to the length of the leaf, into small strips. The cut leaves are transferred to 20 milliliter of a solution containing 0.4 M Mannitol and 10 mM MES, pH 5.7, in a 250 milliliter side armed flask. Additional leaves are cut such that the total number of leaves processed is 100. After all leaves are cut, the solution in the flask is removed with a pipette and 20 milliliter of a cellulase/macerozyme solution is added. The enzyme solution is prepared as follows: 8.6 milliliter of $H_2O$, 10 milliliter of 0.8 M mannitol, and 400 microliter 0.5M MES, pH 5.7, are mixed and heated to 55° C. R-10 cellulase (0.3 g, Serva) and R-10 macerozyme (0.08 g, Serva) are added and the solution is mixed by inversion. The enzyme solution is incubated at room temperature for 10–15 min. A 400 microliter aliquot of 1M KCl and 600 microliter of 1M CaCl2 are added to the enzyme solution, mixed, and the resulting solution is sterile filtered through a 0.2 μM filter. After addition of the enzyme solution, the flask is swirled gently to mix the leaf pieces and a house vacuum is applied for 5 minutes. Prior to releasing the vacuum, the flask is swirled gently to release air bubbles from the leaf cuts. The leaves are digested for 2–3 hours at room temperature.

Protoplasts are released from the leaves by gently swirling the flask for 1 min and the protoplast containing solution is filtered through nylon mesh (62 micron mesh). The eluent is transferred to a sterile, screw top, 40 milliliter conical glass centrifuge tube and centrifuged at 115 g for 2 min. The supernatant is removed with a Pasteur pipette and 10 milliliter ice cold W5 solution is added (W5 solution contains 154 mM NaCl, 125 mM $CaCl_2$, 5 mM KCl, 5 mM glucose, and 1.5 mM MES, pH 5.7). The sample is mixed by rocking the tube end over end until all of the pellet is in solution. The sample is centrifuged as described above and the supernatant is removed with a Pasteur pipette. The protoplast pellet is resuspended in 5 milliliters of ice cold W5. The sample is incubated for 30 minutes on ice so that the protoplasts become competent for transformation. Intact protoplasts are quantitated using a hemacytometer. The protoplasts are isolated by centrifugation and resuspended in an ice cold solution containing 0.4 M mannitol, 15 mM $MgCl_2$, and 5 mM MES, pH 5.7, to approximately $2 \times 10^6$ protoplasts/ millilter.

Plasmid DNA samples (40 micrograms, 1 microgram/ microliter stock) for transformation are placed in 40 milliliter glass conical centrifuge tubes. An aliquot of protoplasts (800 microliter) is added to an individual tube followed immediately by 800 microliter of a solution containing 40% PEG 3350 (w/v), 0.4 M mannitol, and 100 mM Ca $(NO_3)_2$. The sample is mixed by gentle inversion and the procedure is repeated for any remaining samples. All transformation tubes are incubated at room temperature for 30 minutes. Protoplasts samples are diluted sequentially with 1.6 milliliters, 4 milliliters, 8 milliliters protoplasts can be determined by Western detection of the protein. Samples from transient expression experiments are prepared for Western analysis as follows. Protoplasts are harvested by centrifugation (115 g) and the supernatant is removed. An aliquot (14 microliters) of 7× stock of protease inhibitor stock is added to the sample and the sample is brought to a final volume of 100 microliters with a solution containing 0.5 M marmitol, 5 mM MES, pH 5.7, 20 mM KCl, 5 mM CaCl2. The 7× stock of protease inhibitors is prepared by dissolving one "Complete Mini Protease Inhibitor Tablet" (Boehringer Manneheim) in 1.5 milliliter, 0.5 M mannitol, 5 mM MES, pH 5.7, 20 mM KCl, 5 mM $CaCl_2$. The protoplasts are disrupted in a 1.5 milliliter centrifuge tube using a pellet pestle mixer (Kontes) for 30 seconds. Soluble proteins are separated from insoluble proteins by centrifugation at maximum speed in a microcentrifuge (10 min, 4° C.). The protein concentration of the soluble fraction is quantitated using the Bradford dye-binding procedure with bovine serum albumin as a standard (Bradford, M. M. Anal. Biochem. 1976, 72, 248–254). The insoluble protein is resuspended in 100 microliters 1× gel loading buffer (New England Biolabs, Beverly, Mass.) and a volume equal to that loaded for the soluble fraction is prepared for analysis. Samples from the soluble and insoluble fractions of the protoplast transient expression experiment, as well as standards of green fluorescent protein (Clontech, Palo Alto, Calif.), are resolved by SDS-PAGE and proteins are blotted onto PVDF. Detection of transiently expressed proteins can be performed by Western analysis using Living Colors Peptide Antibody to GFP (Clontech, Palo Alto, Calif.), the anti-beta-glucuronidase antibody to GUS (Molecular Probes, Inc., Eugene, Oreg.), and the Immun-Star Chemiluminescent Protein Detection System (BioRad, Hercules, Calif.).

I claim:

1. A DNA construct for expression of multiple gene products in a cell comprising:
   (a) a single promoter at the 5' end of the construct;
   (b) an intein splicing unit comprising two or more extein sequences encoding separate proteins, and one or more intein sequences fused to the carboxy-terminus encoding portion of each extein sequence, except the last extein sequence to be expressed; and
   (c) a 3' termination sequence comprising a polyadenylation signal following the last extein protein coding sequence;
   wherein the intein splicing unit is expressed as a precursor protein containing at least one intein flanked by extein encoded proteins; wherein at least one of the inteins can catalyze excision of the exteins; and wherein at least one amino acid residue is substituted in, or added to, the intein splicing unit so that the excised exteins are not ligated by the intein.

2. The construct of claim 1 wherein the promoter is selected from the group consisting of inducible promoters, constitutive promoters and tissue specific promoters.

3. The construct of claim 1 wherein the extein sequences encoding separate proteins are preceded or followed by a sequence encoding a peptide that targets the gene expression product to a particular compartment within the cell in which the construct is expressed.

4. The construct of claim 1 wherein the proteins are different enzymes.

5. The construct of claim 1 wherein the proteins are the same proteins.

6. The construct of claim 1 wherein the intein splicing unit expression product prevents the ligation reactions normally associated with protein splicing.

7. The DNA construct of claim 6 wherein the DNA construct encodes a glycine or alanine linking the intein and extein amino acid sequences.

8. The construct of claim 1 wherein the promoter is a promoter operable in a plant cell.

9. The construct of claim 8 wherein the proteins are selected from the group consisting of acyl CoA dehydrogenases, acyl CoA oxidases, catalases, alpha subunits of beta-oxidation, beta subunits of beta-oxidation, PHA syntheses with medium chain length substrate specificity, beta-ketothiolases, NADH or NADPH dependent reductases, PHA synthases with short chain length specificity, and PHA synthases that incorporate both short and medium chain length substrates.

10. The construct of claim 8 wherein the proteins are selected from the group consisting of enzymes encoded by the phaG locus, medium chain length syntheses, beta-ketothiolases, NADH or NADPH dependent reductases, and PHA synthases that incorporate both short and medium chain length substrates.

11. The construct of claim 8 wherein the proteins are selected from the group consisting of herbicide resistance, insect resistance, and marker proteins.

12. A method for expressing multiple genes in cells comprising transforming the cells with a DNA construct comprising:

(a) a single promoter at the 5' end of the construct;

(b) an intein splicing unit comprising two or more extein sequences encoding separate proteins, and one or more intein sequences fused to the carboxy-terminus encoding portion of each extein sequence, except the last extein sequence to be expressed; and (c) a 3' termination sequence comprising a polyadenylation signal following the last extein protein coding sequence;

wherein the intein splicing unit is expressed as a precursor protein containing at least one intein flanked by extein encoded proteins; wherein at least one of the inteins can catalyze excision of the exteins; and wherein at least one amino acid residue is substituted in, or added to, the intein splicing unit so that the excised exteins are not ligated by the intein.

13. The method of claim 12 wherein the cell is plant cell and the promoter is a promoter operable in a plant cell.

14. The method of claim 12 wherein the promoter is selected from the group consisting of inducible promoter, constitutive promoters and tissue specific promoter.

15. The method of claim 12 wherein the extein sequences encoding separate proteins are preceded or followed by a sequence encoding a peptide that targets the gene expression product to a particular compartment within the cell in which the construct is expressed.

16. The method of claim 12 wherein the proteins are different enzymes.

17. The method of claim 12 wherein the proteins are the same proteins.

18. The method of claim 12 wherein the intein splicing unit expression product prevents the ligation reactions normally associated with protein splicing.

19. The method of claim 18 wherein the DNA construct encodes a glycine or alanine linking the intein and axiom amino acid sequences.

20. The method of claim 13 for making polyhydroxyalkanoates in plants wherein the proteins are selected from the group consisting of acyl CoA dehydrogenases, acyl CoA oxidases, catalases, alpha subunits of beta-oxidation, beta subunits of beta-oxidation, PHA synthases with medium chain length substrate specificity, beta-ketothiolases, NADH or NADPH dependent reductases, PHA synthases with short chain length specificity, and PHA synthases that incorporate both short and medium chain length substrates.

21. The method of claim 13 for making polyhydroxyalkanoate in plants wherein the proteins are selected from the group consisting of enzymes encoded by the phaG locus, medium chain length synthases, beta-ketothiolases, NADH or NADPH dependent reductases, and PHA syntheses that incorporate both short and medium chain length substrates.

22. The method of claim 13 wherein the proteins are selected from the group consisting of herbicide resistance, insect resistance, and marker proteins.

\* \* \* \* \*

UNITED STATES PATENT AND TRADEMARK OFFICE
CERTIFICATE OF CORRECTION

PATENT NO. : 7,026,526 B2  Page 1 of 1
APPLICATION NO. : 09/779957
DATED : April 11, 2006
INVENTOR(S) : Kristi D. Snell It is certified that error appears in the above-identified patent and that said Letters Patent is hereby corrected as shown below:

Claim 9, column 16, line 57, replace "syntheses" with --synthases--.
Claim 10, column 16, line 64, replace "syntheses" with --synthases--.
Claim 14, column 17, line 27, replace "promoter" with --promoters--.
Claim 14, column 17, line 28, replace "promoter" with --promoters--.
Claim 19, column 18, line 10, replace "axiom" with --extein--.
Claim 21, column 18, lines 22-23, replace "polyhydroxyalkanoate" with --polyhydroxyalkanoates--.
Claim 21, column 18, line 26, replace "syntheses" with --synthases--.

Signed and Sealed this

Sixteenth Day of October, 2007

JON W. DUDAS
*Director of the United States Patent and Trademark Office*

SEQUENCE LISTING

<160> NUMBER OF SEQ ID NOS: 2

<210> SEQ ID NO 1
<211> LENGTH: 1617
<212> TYPE: DNA
<213> ORGANISM: Pyrococcus sp.
<220> FEATURE:
<221> NAME/KEY: misc_feature
<222> LOCATION: (1)..(3)
<223> OTHER INFORMATION: Asparagine residue encoded at N-terminal extein
      junction point
<221> NAME/KEY: misc_feature
<222> LOCATION: (1615)..(1617)
<223> OTHER INFORMATION: Serine residue encoded at C-terminal extein
      junction point

<400> SEQUENCE: 1

```
aacagcattt taccggaaga atgggttcca ctaattaaaa acggtaaagt taagatattc      60
cgcattgggg acttcgttga tggacttatg aaggcgaacc aaggaaaagt gaagaaaacg     120
ggggatacag aagttttaga agttgcagga attcatgcgt tttcctttga caggaagtcc     180
aagaaggccc gtgtaatggc agtgaaagcc gtgataagac accgttattc cggaaatgtt     240
tatagaatag tcttaaactc tggtagaaaa ataacaataa cagaagggca tagcctattt     300
gtctatagga acggggatct cgttgaggca actggggagg atgtcaaaat tggggatctt     360
cttgcagttc caagatcagt aaacctacca gagaaaaggg aacgcttgaa tattgttgaa     420
cttcttctga atctctcacc ggaagagaca gaagatataa tacttacgat tccagttaaa     480
ggcagaaaga acttcttcaa gggaatgttg agaacattac gttggatttt tggtgaggaa     540
aagagagtaa ggacagcgag ccgctatcta agacaccttg aaaatctcgg atacataagg     600
ttgaggaaaa ttggatacga catcattgat aaggaggggc ttgagaaata tagaacgttg     660
tacgagaaac ttgttgatgt tgtccgctat aatggcaaca agagagagta tttagttgaa     720
tttaatgctg tccgggacgt tatctcacta atgccagagg aagaactgaa ggaatggcgt     780
attggaacta gaaatggatt cagaatgggt acgttcgtag atattgatga agattttgcc     840
aagcttcttg gctactatgt gagcgaggga agtgcgagga agtggaagaa tcaaactgga     900
ggttggagtt acactgtgag attgtacaac gagaacgatg aagttcttga cgacatgaa      960 cacttagcca agaagttttt tgggaaagtc aaacgtggaa agaactatgt tgagatacca    1020
aagaaaatgg cttatatcat cttgagagc ctttgtggga ctttggcaga aaacaaaagg    1080
gttcctgagg taatctttac ctcatcaaag ggcgttagat gggccttcct tgagggttat    1140
ttcatcggcg atggcgatgt tcacccaagc aagagggttc gcctatcaac gaagagcgag    1200 ctttttagtaa atggccttgt tctcctactt aactcccttg gagtatctgc cattaagctt    1260
ggatacgata gcggagtcta cagggtttat gtaaacgagg aacttaagtt tacggaatac    1320
agaaagaaaa agaatgtata tcactctcac attgttccaa aggatattct caaagaaact    1380
```

```
-continued tttggtaagg tcttccagaa aaatataagt tacaagaaat ttagagagct tgtagaaaat    1440
ggaaaacttg acagggagaa agccaaacgc attgagtggt tacttaacgg agatatagtc    1500
ctagatagag tcgtagagat taagagagag tactatgatg gttacgttta cgatctaagt    1560
gtcgatgaag atgagaattt ccttgctggc tttggattcc tctatgcaca taatagc       1617

<210> SEQ ID NO 2
<211> LENGTH: 600
<212> TYPE: DNA
<213> ORGANISM: Mycobacterium xenopi
<220> FEATURE:
<221> NAME/KEY: misc_feature
<222> LOCATION: (1)..(3)
<223> OTHER INFORMATION: Tyrosine residue encoded at N-terminal extein
      junction point
<221> NAME/KEY: misc_feature
<222> LOCATION: (558)..(600)
<223> OTHER INFORMATION: Threonine residue encoded at C-terminal extein
      junction point

<400> SEQUENCE: 2
tactgcatca cgggagatgc gctggttgcc ctacccgagg gcgagtcggt acgcatcgcc      60
gacatcgtgc cgggtgcgcg gcccaacagt gacaacgcca tcgacctgaa agtccttgac    120
cggcatggca atcccgtgct cgccgaccgg ctgttccact ccggcgagca tccggtgtac    180
acggtgcgta cggtcgaagg tctgcgtgtg acggcaccg cgaaccaccc gttgttgtgt    240
ttggtcgacg tcgccggggt gccgacccctg ctgtggaagc tgatcgacga aatcaagccg    300
ggcgattacg cggtgattca acgcagcgca ttcagcgtcg actgtgcagg tttttgcccgc    360 ggaaaacccg aatttgcgcc cacaacctac acagtcggcg tccctggact ggtgcgtttc    420
ttggaagcac accaccgaga cccggacgcc caagctatcg ccgacgagct gaccgacggg    480
cggttctact acgcgaaagt cgccagtgtc accgacgccg gcgtgcagcc ggtgtatagc    540
cttcgtgtcg acacggcaga ccacgcgttt atcaccaacg ggttcgtcag ccacaacacc    600
```